(12) United States Patent
Kameyama et al.

(10) Patent No.: US 9,056,119 B2
(45) Date of Patent: Jun. 16, 2015

(54) VEGF PRODUCTION PROMOTER

(75) Inventors: Akiyo Kameyama, Kawachi-gun (JP); Sachie Ueda, Utsunomiya (JP)

(73) Assignee: Kao Corporation, Tokyo (JP)

( * ) Notice: Subject to any disclaimer, the term of this patent is extended or adjusted under 35 U.S.C. 154(b) by 111 days.

(21) Appl. No.: 13/805,798

(22) PCT Filed: Jul. 1, 2011

(86) PCT No.: PCT/JP2011/065189
§ 371 (c)(1),
(2), (4) Date: Dec. 20, 2012

(87) PCT Pub. No.: WO2012/002536
PCT Pub. Date: Jan. 5, 2012

(65) Prior Publication Data
US 2013/0102549 A1    Apr. 25, 2013

(30) Foreign Application Priority Data

Jul. 2, 2010 (JP) ................................. 2010-152195

(51) Int. Cl.
*A61K 31/704* (2006.01)
*A61K 8/63* (2006.01)
*A61K 31/7048* (2006.01)
*A61Q 5/00* (2006.01)
*A61Q 19/00* (2006.01)
*C07J 71/00* (2006.01)

(52) U.S. Cl.
CPC ................. *A61K 31/704* (2013.01); *A61K 8/63* (2013.01); *A61K 31/7048* (2013.01); *A61K 2800/78* (2013.01); *A61Q 5/00* (2013.01); *A61Q 19/00* (2013.01); *C07J 71/00* (2013.01)

(58) Field of Classification Search
None
See application file for complete search history.

(56) References Cited

FOREIGN PATENT DOCUMENTS

| CN | 1099287 C | * | 1/2003 |
|---|---|---|---|
| CN | 101057854 B | | 5/2010 |
| JP | 09-030977 A | | 2/1997 |
| JP | 11-286432 A | | 10/1999 |
| JP | 2000-212059 A | | 8/2000 |
| JP | 2004-035443 A | | 2/2004 |
| JP | 2004-043393 A | | 2/2004 |
| JP | 2006-160698 A | | 6/2006 |
| JP | 2006-342068 A | | 12/2006 |
| JP | 2007-291042 A | | 11/2007 |
| JP | 2008-222671 A | | 9/2008 |
| JP | 2010-143862 A | | 7/2010 |
| KR | 10-2011-0002198 | | 1/2011 |

OTHER PUBLICATIONS

CN1099287 C, Jan. 22, 2003, machine translation.*
Kimura, Photochemistry and Photobiology, 2010, 86: 955-963, abstract only.*
International Search Report (ISR) for PCT/JP2011/065189, I.A. fd: Jul. 1, 2011, mailed Aug. 2, 2011 from the Japanese Patent Office, Tokyo, Japan.
International Preliminary Report on Patentability (IPRP), Chapter I of the Patent Cooperation Treaty, including the Written Opinion for PCT/JP2011/065189, I.A. fd: Jul. 1, 2011, issued Feb. 12, 2013, from the International Bureau of WIPO, Geneva, Switzerland.
Detmar, M., "The role of VEGF and thrombospondins in skin angiogenesis," J Dermatological Sci 24 (Supp. 1): S78-S84 (2000), Elsevier, Amsterdam, Netherlands.
Yano, K et al., "Control of hair growth and follicle size by VEGF-mediated angiogenesis," J Clin Invest 107(4): 409-417, (Feb. 2001), Am. Soc. for Clinical Investigation, Ann Arbor, MI.
Matsuhashi, Y et al., "Characteristics of the nucleosidic transport antagonism of Cimicifugoside," Proceedings of the $121^{st}$ Annual Meeting of the Pharmaceutical Society of Japan, vol. 4, p. 54, Abstract 28 [PE] I-014, Sapporo, Japan, Mar. 28, 2001, The Pharmaceutical Society of Japan, Tokyo, Japan.
Takahira, M et al., "Antimalarial activity and nucleoside transport inhibitory activity of the triterpenic constituents of *Cimicifuga* spp.," Biol Pharm Bull 21(8):823-828, (Aug. 1998), Pharmaceutical Society of Japan, Tokyo, Japan.
Moriwaki, S et al., "The present status and prospective problem of hair grower, 'A search of molecules relating to hair aging and an effect of eucalyptus extract on VEGF transcription,'" Fragrance J 35(12):22-27 (2007), Fragrance Journal Ltd., Tokyo, Japan.
Kusano, A et al., "Studies on the constituents of *Cimicifuga* species. XXVI. Twelve new cycloanostanol glycosides from the underground parts of *Cimicifuga simplex* Wormsk," Chem. Pharm. Bull 47(4):511-516 (1999), Pharmaceutical Society of Japan, Tokyo, Japan.
He, K et al., "*Cimicifuga* species identification by high performance liquid chromatography-photodiode array/mass spectrometric/evaporative light scattering detection for quality control of black cohosh products," J Chromatogr A 1112(1-2): 241-254, (Apr. 2006), Elsevier, Amsterdam, Netherlands.
Li, W et al., "High-performance, liquid chromatographic analysis of Black Cohosh (*Cimicifuga racemosa*) constituents with in-line evaporative light scattering and photodiode array detection," Analytica Chimica Acta 471:61-75 (2002), Elsevier, Amsterdam, Netherlands.
Gaube, F et al., "Gene expression profiling reveals effects of *Cimicifuga racemose* (L.) NUTT. (black cohosh) on the estrogen receptor positive human breast cancer cell line MCF-7," BMC Pharmacology 7:11 (Sep. 2007), doi:10.1 186/1471-2210-7-11, Biomed Central Open Access, 19 pages.
Maruzen Pharmaceuticals Co., Ltd, "Ikumo Sayo Shokubutsu Extract"Biwaha Extract CA, Fragrance J 35(1):124-125, (2007), Fragrance Journal Ltd., Tokyo, Japan.
Extended European search report, including the supplementary European search report and the European search opinion, for EP Appl. No. 11800998.4, dated Sep. 23, 2014, European Patent Office, Munich, Germany.

* cited by examiner

*Primary Examiner* — Layla Bland
(74) *Attorney, Agent, or Firm* — Sterne, Kessler, Goldstein & Fox P.L.L.C.

(57) ABSTRACT

Provided are a VEGF production promoter, a hair quality improver, and an external preparation for skin, each of which has a VEGF production promoting activity and can be used as a pharmaceutical agent, a cosmetic, a food, or a material therefor.
The VEGF production promoter, the hair quality improver, and the external preparation for skin each comprises, as an active ingredient, a cycloartane-type glycoside represented by the following general formula (1) (where R represents a xylose residue or an arabinose residue, and the ring D moiety represents any one of the following moieties a to f (where $R_1$ represents a hydrogen atom or a methyl group, $R_2$ represents a hydrogen atom or an acetyl group, $R_3$ represents a hydrogen atom or a hydroxyl, group, $R_4$ represents a hydrogen atom or a hydroxyl group, and Ac represents an acetyl group)).
(1)
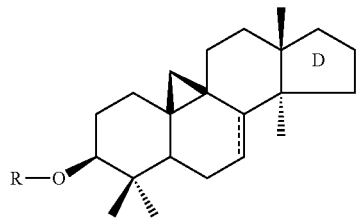
(a)
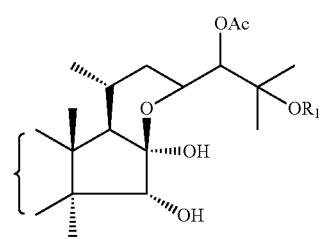
(b)
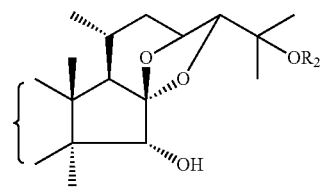
(c)
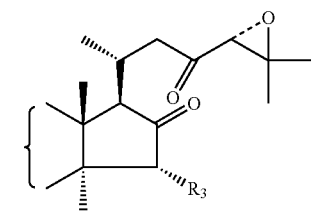
-continued
(d)
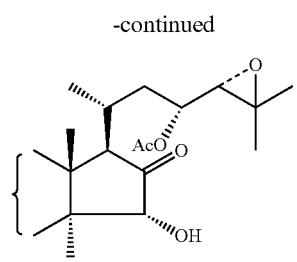
(e)
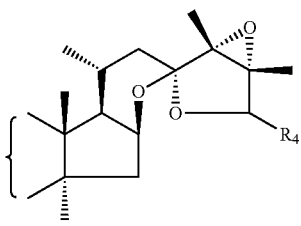
(f)
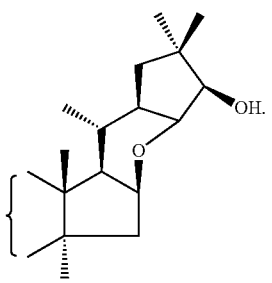
16 Claims, No Drawings

VEGF PRODUCTION PROMOTER

FIELD OF THE INVENTION

The present invention relates to a VEGF production promoter, a hair quality improver, and an external preparation for skin, each of which can promote production of vascular endothelial growth factor (VEGF).

BACKGROUND OF THE INVENTION

VEGF is known as vascular permeability factor but recent studies report that VEGF is major angiogenesis factor in human skin. Therefore, VEGF is a molecule which attracts attention in fields of studies on healing of wound, improvement of skin color, hair growing/hair restoration, and the like.

In normal skin, VEGF is secreted from epidermal keratinocytes in a small amount and is bound to a specific receptor which is present on dermal microvascular endothelial cells. As a result, viability of the endothelial cells is kept to maintain upper blood vessels having reticular structures.

It has been reported that VEGF in the epidermis thickened during inflammation or healing of wound is very highly expressed, which leads to an increase in blood vessels and supply of nutrients (Non Patent Document 1). Further, it has been reported that, in the hair anagen phase, blood vessels around the hair follicle are drastically dilated and VEGF is expressed in cells of the hair follicle, while in the hair catagen and telogen phases, expression of VEGF is suppressed by regression of the blood vessels (Non Patent Document 2).

It has further been reported that VEGF promotes vascular formation, and hence promotes blood circulation to supply large amounts of nutrients to hair roots and is related to adhesion between hair cortex cells.

In particular, a recent study reports that a decrease in VEGF expression level is correlated with a decrease in hair firmness and elasticity, and application of a VEGF production promoter to a hair cosmetic has been a focus of attention (Non Patent Document 5).

Therefore, promotion of production of VEGF, which is involved in the increase in blood vessels and supply of nutrients in the dermis is very effective not only for recovery/healing of wound but also for improvement of skin color such as dullness or decreased transparency of skin caused by lowered skin metabolism or the like. In addition, promotion of production of VEGF, which is also involved in growth of hair/hair follicle is effective for prevention and improvement of symptoms such as hair loss/thin hair and decreased hair firmness and elasticity.

In view of the foregoing, various VEGF production promoters have been developed so far. For example, the following preparation and extracts have been reported to have VEGF production promoting activities: a preparation derived from soybean (Patent Document 1); an extract of each of *Boletinus cavipes, Suillus laricinus, Suillus grevillei, Boletinus asiaticus, Suillus bovinus, Suillus spectabilis, Acanthopanax senticosus* Harms, polygonatum rhizome, *Gentiana lutea*, Alexandrian Senna, *Eucommia ulmoides*, rhubarb, melilot, coix seed, Chinese wolfberry fruit, Japanese Angelica Root, rehmannia root, gardenia fruit, *Glycyrrhiza*, carrot, red ginseng, lithospermum root, and cymbidium (Patent Document 2); an extract of a plant belonging to the genus *Pandanus* (*Pandanus* L.f.) (Patent Document 3); and an extract of each of shiitake mushroom, *Echinacea purpurea*, prune, bean sprouts, and jiaogulan (Patent Document 4). However, blending of each of the VEGF production promoters may be limited from the viewpoint of a side effect, and blending of each of the promoters in an effective amount may cause a problem such as coloring or unpleasant odor.

On the other hand, it has been reported that the cycloartane-type glycoside is isolated from a plant belonging to the genus *Cimicifuga* of the family Ranunculaceae such as *Cimicifuga simplex* and has pharmacological activities such as an thymidine intake inhibitory activity (Non Patent Document 3) and an antimalarial activity (Non Patent Document 4).

However, it was not known that the cycloartane-type glycoside has any VEGF production promoting activity.

CITATION LIST

Patent Document

[Patent Document 1] JP-A-11-286432

[Patent Document 2] JP-A-2000-212059

[Patent Document 3] JP-A-2004-43393

[Patent Document 4] JP-A-2004-35443

Non Patent Document

[Non Patent Document 1] Detmar M. The role of VEGF and thrombospondins in skin angiogenesis, J Dermatol Sci. 24 (Suppl 1) S78-84, 2000

[Non Patent Document 2] Yano K, Brown; L F, Detmar M. Control of hair growth and hair follicle size by VEGF-mediated angiogenesis, J Clin Invest. 107(4), 409-17, 2001

[Non Patent Document 3] Matsuhashi, Kusano and others, Proceedings of the 121st Annual Meeting of the Pharmaceutical Society of Japan, Vol. 4, p 54

[Non Patent Document 4] Takahira M., Bio. Pharm. Bull., 21, 823-828 (1998)

[Non Patent Document 5] Moriwaki, Taguchi, Fragrance Journal, No. 12, 2007

SUMMARY OF THE INVENTION

The present invention relates to the following items 1) to 9).

1) A VEGF production promoter, comprising, as an active ingredient, a cycloartane-type glycoside represented by the following general formula (1)

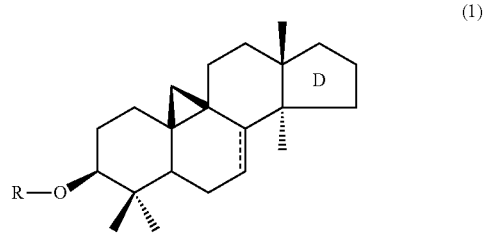

(1)

where R represents a xylose residue or an arabinose residue, and the ring D moiety represents any one of the following moieties a to f:

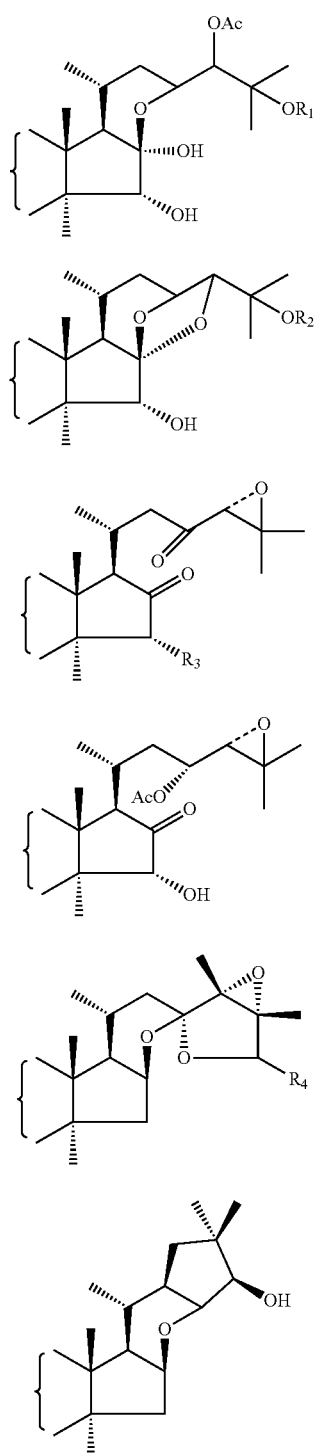

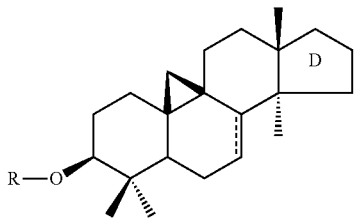

where R represents a xylose residue or an arabinose residue, and the ring D moiety represents any one of the following moieties a to f:

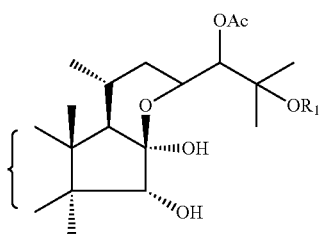

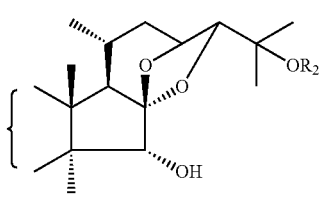

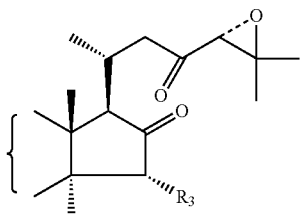

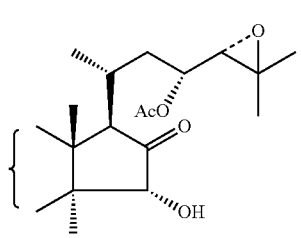

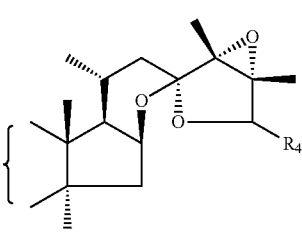

where $R_1$ represents a hydrogen atom or a methyl group, $R_2$ represents a hydrogen atom or an acetyl group, $R_3$ represents a hydrogen atom or a hydroxyl group, $R_4$ represents a hydrogen atom or a hydroxyl group, and Ac represents an acetyl group.

2) A hair quality improver, comprising, as an active ingredient, a cycloartane-type glycoside represented by the following general formula (1)

-continued

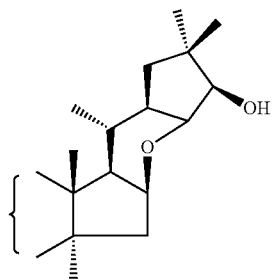
(f)

where $R_1$ represents a hydrogen atom or a methyl group, $R_2$ represents a hydrogen atom or an acetyl group, $R_3$ represents a hydrogen atom or a hydroxyl group, $R_4$ represents a hydrogen atom or a hydroxyl group, and Ac represents an acetyl group.

3) An external preparation for skin, comprising a cycloartane-type glycoside represented by the following general formula (1):

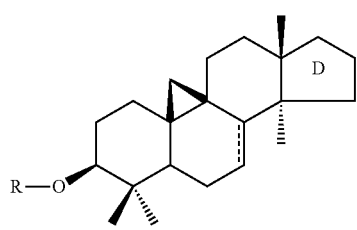
(1)

where R represents a xylose residue or an arabinose residue, and the ring D moiety represents any one of the following moieties a to f:

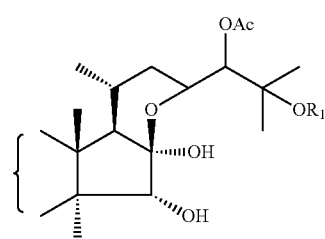
(a)

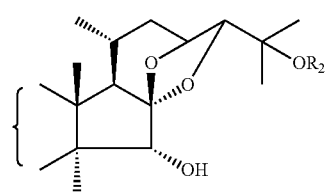
(b)

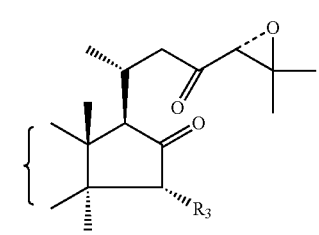
(c)

-continued

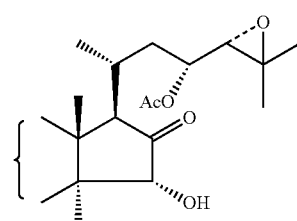
(d)

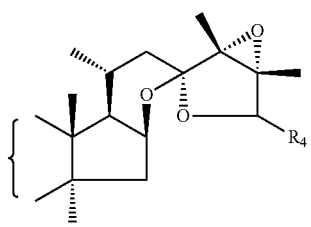
(e)

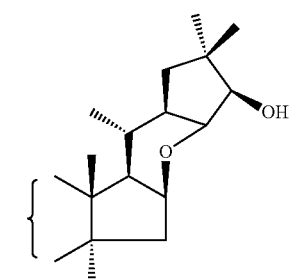
(f)

where $R_1$ represents a hydrogen atom or a methyl group, $R_2$ represents a hydrogen atom or an acetyl group, $R_3$ represents a hydrogen atom or a hydroxyl group, $R_4$ represents a hydrogen atom or a hydroxyl group, and Ac represents an acetyl group.

4) A method of promoting VEGF production, comprising administering or taking a cycloartane-type glycoside represented by the following general formula (1):

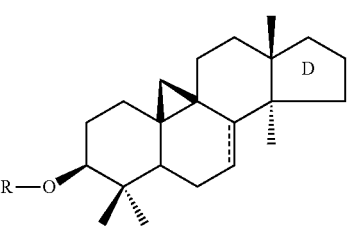
(1)

where R represents a xylose residue or an arabinose residue, and the ring D moiety represents any one of the following moieties a to f:

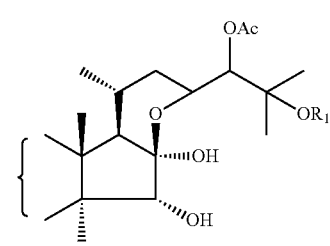
(a)

(b)
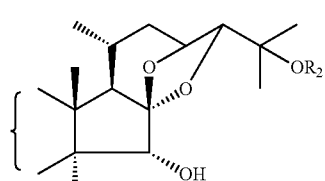

(c)
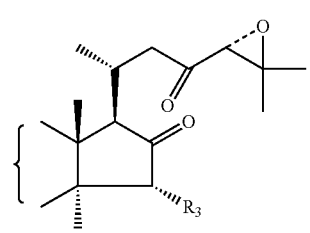

(d)
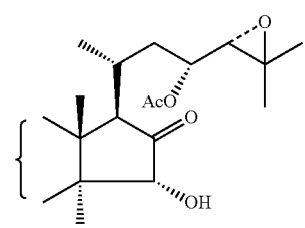

(e)
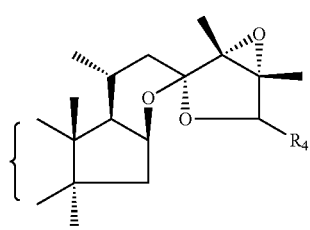

(f)
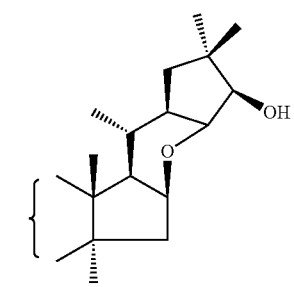

where $R_1$ represents a hydrogen atom or a methyl group, $R_2$ represents a hydrogen atom or an acetyl group, $R_3$ represents a hydrogen atom or a hydroxyl group, $R_4$ represents a hydrogen atom or a hydroxyl group, and Ac represents an acetyl group.

5) A method of improving hair quality, comprising administering or taking a cycloartane-type glycoside represented by the following general formula (1):

(1)
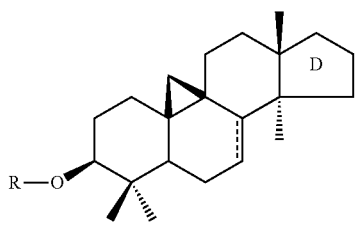

where R represents a xylose residue or an arabinose residue, and the ring D moiety represents any one of the following moieties a to f:

(a)
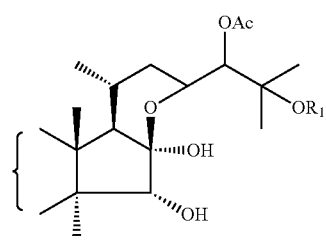

(b)
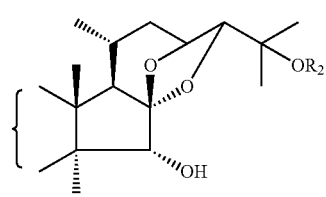

(c)
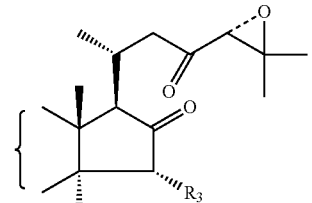

(d)
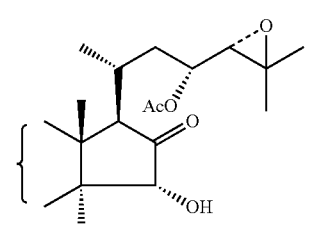

(e)
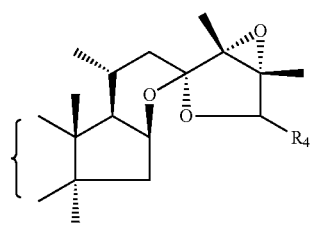

-continued (f)
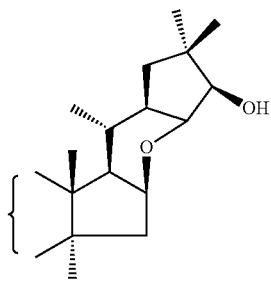

where R₁ represents a hydrogen atom or a methyl group, R₂ represents a hydrogen atom or an acetyl group, R₃ represents a hydrogen atom or a hydroxyl group, R₄ represents a hydrogen atom or a hydroxyl group, and Ac represents an acetyl group.

6) Use of a cycloartane-type glycoside represented by the following general formula (1) for manufacturing a VEGF production promoter:

(1)
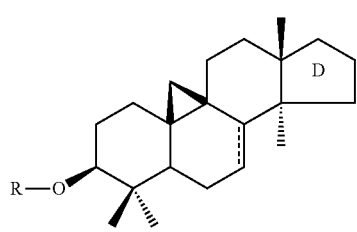

where R represents a xylose residue or an arabinose residue, and the ring D moiety represents any one of the following moieties a to f:

(a)
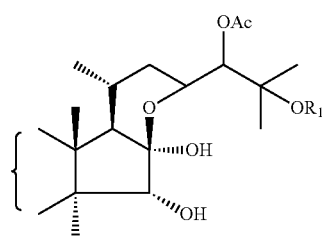

(b)
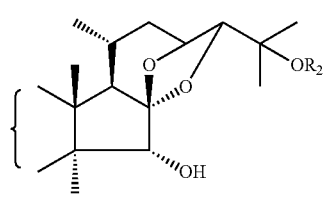

(c)
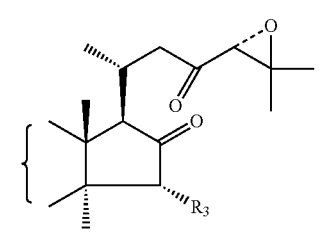

-continued (d)
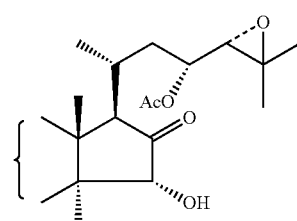

(e)
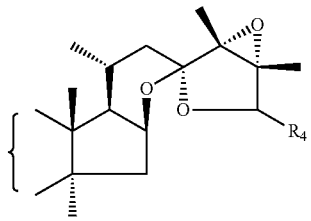

(f)
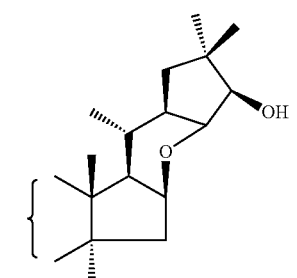

where R₁ represents a hydrogen atom or a methyl group, R₂ represents a hydrogen atom or an acetyl group, R₃ represents a hydrogen atom or a hydroxyl group, R₄ represents a hydrogen atom or a hydroxyl group, and Ac represents an acetyl group.

7) Use of a cycloartane-type glycoside represented by the following general formula (1) for manufacturing a hair quality improver:

(1)
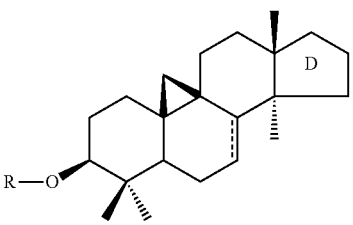

where R represents a xylose residue or an arabinose residue, and the ring D moiety represents any one of the following moieties a to f:

(a)
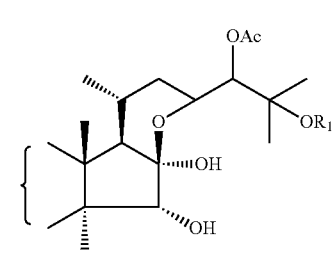

-continued

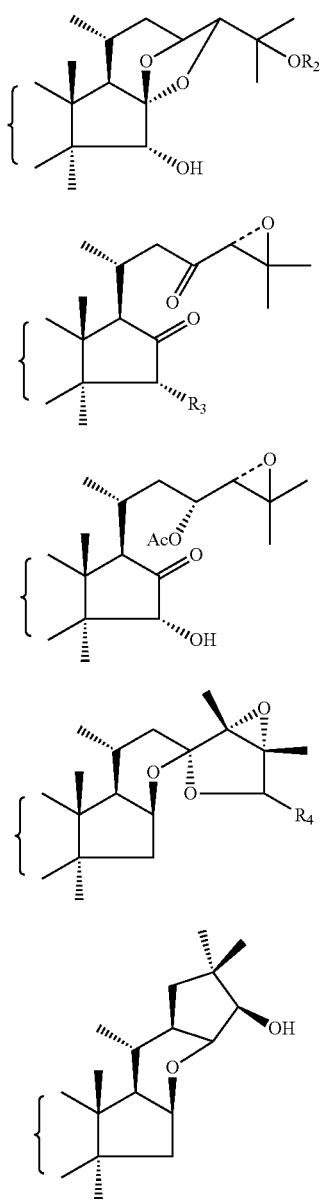

where $R_1$ represents a hydrogen atom or a methyl group, $R_2$ represents a hydrogen atom or an acetyl group, $R_3$ represents a hydrogen atom or a hydroxyl group, $R_4$ represents a hydrogen atom or a hydroxyl group, and Ac represents an acetyl group.

8) A cycloartane-type glycoside represented by the following general formula (1) for use in promoting VEGF production:

(1)

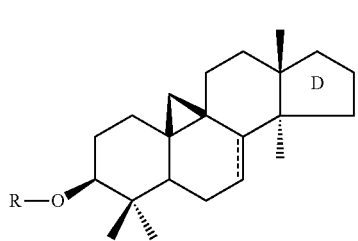

where R represents a xylose residue or an arabinose residue, and the ring D moiety represents any one of the following moieties a to f:

(a)

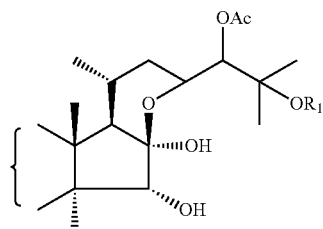

(b)

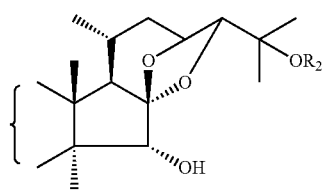

(c)

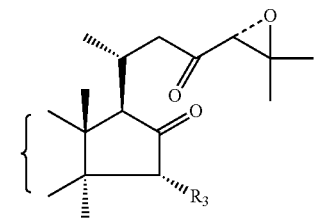

(d)

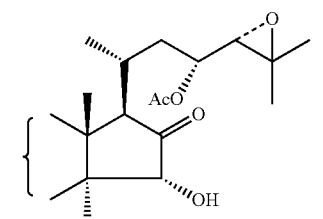

(e)

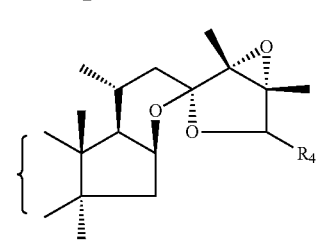

(f)

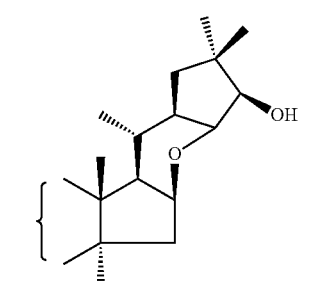

where $R_1$ represents a hydrogen atom or a methyl group, $R_2$ represents a hydrogen atom or an acetyl group, $R_3$ represents a hydrogen atom or a hydroxyl group, $R_4$ represents a hydrogen atom or a hydroxyl group, and Ac represents an acetyl group.

9) A cycloartane-type glycoside represented by the following general formula (1) for use in improving hair quality:

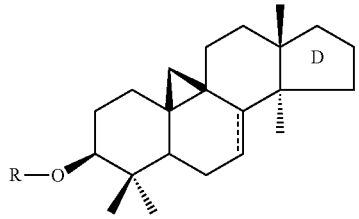
(1)

where R represents a xylose residue or an arabinose residue, and the ring D moiety represents any one of the following moieties a to f:

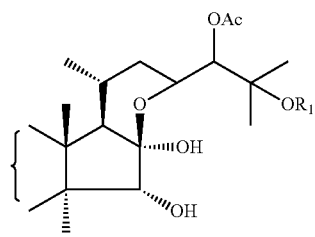
(a)

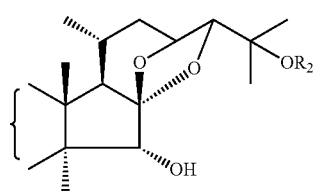
(b)

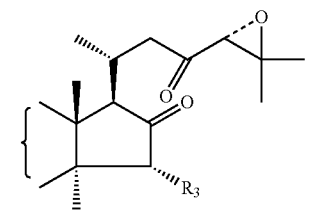
(c)

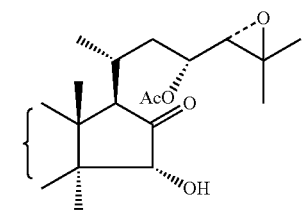
(d)

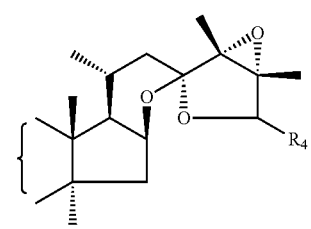
(e)

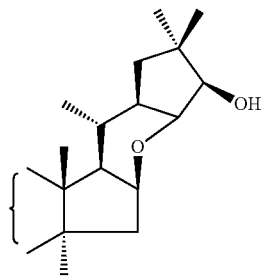
(f)

where $R_1$ represents a hydrogen atom or a methyl group, $R_2$ represents a hydrogen atom or an acetyl group, $R_3$ represents a hydrogen atom or a hydroxyl group, $R_4$ represents a hydrogen atom or a hydroxyl group, and Ac represents an acetyl group.

DETAILED DESCRIPTION OF THE INVENTION

The present invention relates to the provision of a VEGF production promoter, a hair quality improver, and an external preparation for skin, each of which has a VEGF production promoting activity and can be used as a pharmaceutical agent, a cosmetic, a food, or a material therefor.

The inventors of the present invention have made intensive studies on a substance capable of promoting the production of VEGF. As a result, the inventors have found that a specific cycloartane-type glycoside has an excellent VEGF production promoting activity.

According to the present invention, it is possible to provide a pharmaceutical agent, a quasi-drug, a cosmetic, a food, or the like which has an excellent VEGF production promoting activity and is useful for healing of wound, improvement of skin color, hair growing/hair restoration, improvement of hair firmness and elasticity, and the like.

The cycloartane-type glycoside of the present invention is classified into the following six types based on the type of the ring D in the steroid skeleton.

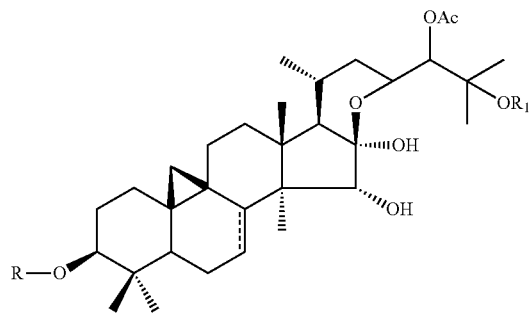

Hydroshengmanol type

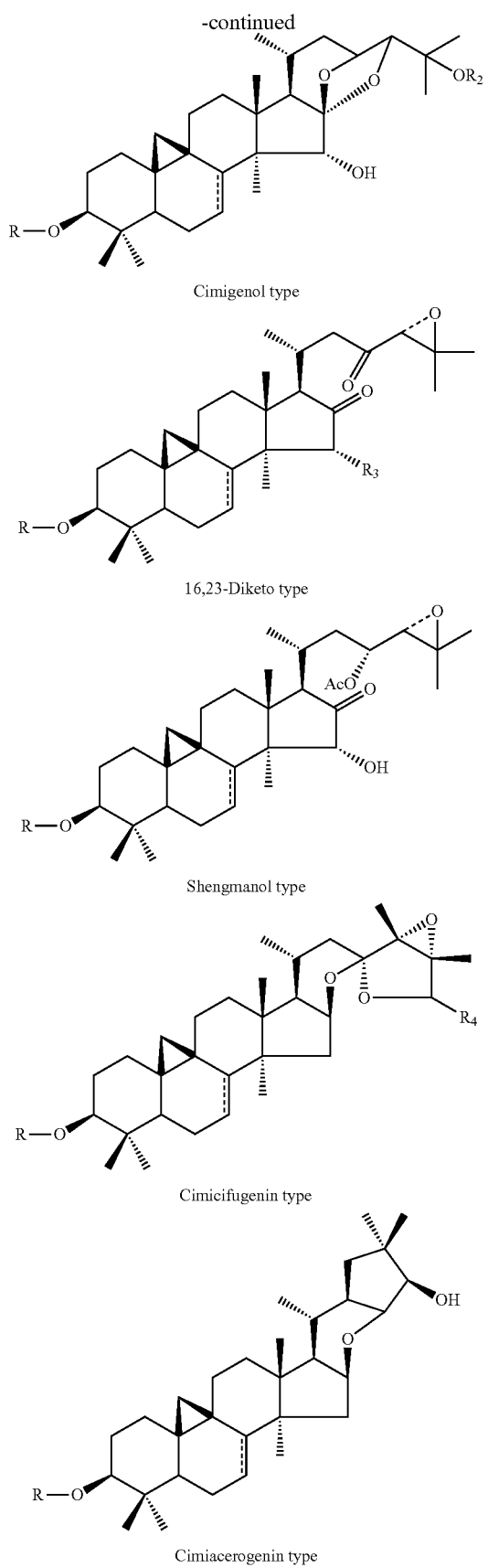

Cimigenol type 16,23-Diketo type

Shengmanol type

Cimicifugenin type

Cimiacerogenin type (In the formulae, R represents a xylose residue or an arabinose residue, $R_1$ represents a hydrogen atom or a methyl group, $R_2$ represents a hydrogen, atom or an acetyl group, $R_3$ represents a hydrogen atom or a hydroxyl group, $R_4$ represents a hydrogen atom or a hydroxyl group, and Ac represents an acetyl group.)

Of those, from the viewpoint of promotion of VEGF production, cycloartane-type glycosides of a hydroshengmanol type, a cimigenol type, and a 16,23-diketo type are preferred.

R represents a xylose residue or an arabinose residue, preferably a xylose residue. Further, the compound may have a stereoisomeric form of α-coordination or β-coordination, preferably β-coordination.

More preferable examples of the cycloartane-type glycoside of the present invention include 7,8-didehydro-24-O-acetylhydroshengmanol-3-O-β-xyloside, 24-epi-7,8-didehydrocimigenol-3-xyloside, and cimicifugoside H-1 represented by the following formulae.

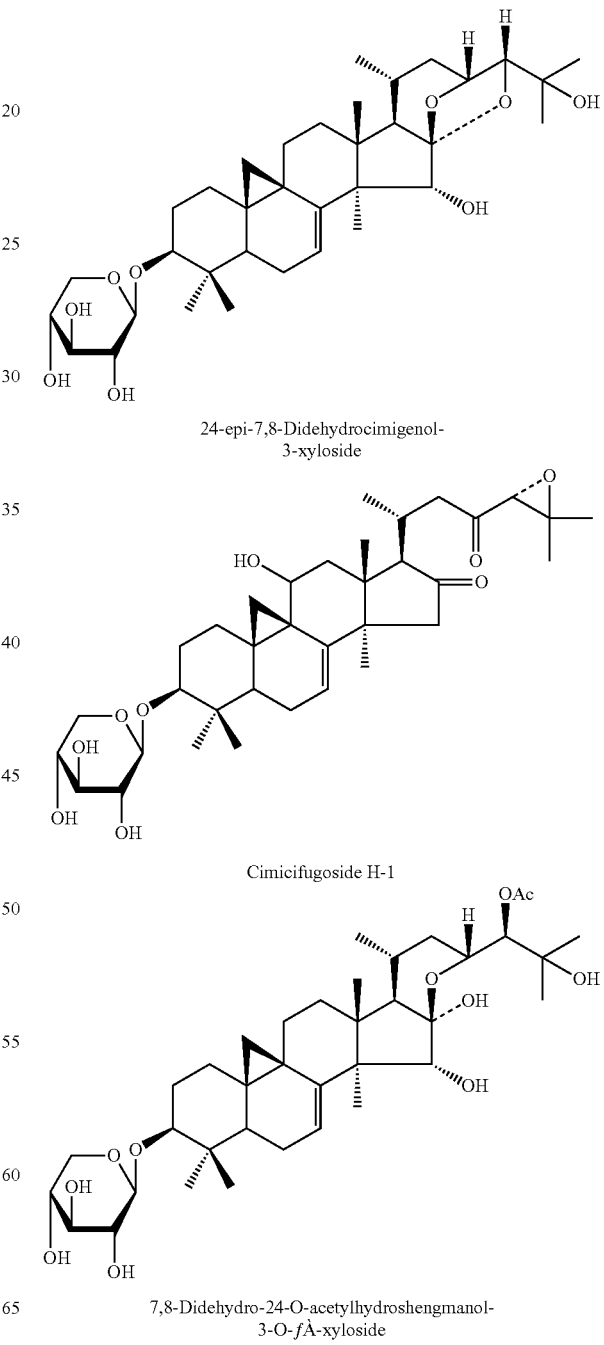

24-epi-7,8-Didehydrocimigenol-3-xyloside

Cimicifugoside H-1

7,8-Didehydro-24-O-acetylhydroshengmanol-3-O-*f*À-xyloside

The cycloartane-type glycoside of the present invention may be obtained by extraction and purification of a plant body. The extraction and purification of a plant body is carried out by, for example, subjecting a root of a plant belonging to the genus *Cimicifuga* of the family Ranuncuilaceae, specifically, *Cimicifuga simplex, C. japonica, C. acerina, C. dahurica, C. heracleifolia* (*Cimicifuga heracleifolia*), *C. foetida, Cimicifuga racemosa* (black cohosh), or the like to solvent extraction and then separating and purifying the extract by appropriate separation and purification means such as column chromatography, ion-exchange chromatography, or high performance liquid chromatography. Hereinafter, examples of isolation of 7,8-didehydro-24-O-acetylhydroshengmanol-3-O-β-xyloside, 24-epi-7,8-didehydrocimigenol-3-xyloside, and cimicifugoside H-1 described above are shown.

1) 99.5% ethanol is added to a shredded product of the root of *Cimicifuga simplex*, and extraction is carried out with stirring, followed by filtration, to thereby obtain an extract of *Cimicifuga simplex*.

2) The solvent of the extract of *Cimicifuga simplex* obtained in 1) is distilled off, and the resultant solid matter is subjected to liquid-liquid distribution with ethyl acetate-water, followed by concentration of the ethyl acetate layer, to thereby obtain solid matter.

3) The solid matter obtained in 2) is charged to a silica gel column, and elution is carried out with a hexane-ethyl acetate mixed solvent and subsequently methanol, to thereby obtain three fractions.

4) The methanol eluted fraction obtained in 3) is charged to a silica gel column again, and elution is carried out with a chloroform-methanol mixed solvent, to thereby obtain 12 fractions.

5) The 12 fractions obtained in 4) are further fractionated by ODS-HPLC (acetonitrile-water mixed solvent), to thereby isolate 24-epi-7,8-didehydrocimigenol-3-xyloside, cimicifugoside H-1, and 7,8-didehydro-24-O-acetyl hydroshengmanol-3-O-β-xyloside.

It should be noted that, according to such extraction and fractionation, the cycloartane-type glycoside may be obtained singly or as a mixture of several types of the compounds. In the VEGA production promoter of the present invention, any of them may be used.

The resultant cycloartane-type glycoside may be used directly, or may be diluted with an appropriate solvent to prepare a diluted solution or may be prepared into a concentrated extract, dried powder, or a paste. Further, the resultant may be freeze-dried, and the freeze-dried product may be diluted with a solvent which is usually used in extraction, such as water, ethanol, or a water/ethanol mixed liquid before use. In addition, the resultant may be encapsuled in, for example, a vehicle such as a liposome or a microcapsule.

As mentioned in Examples to be described later, the cycloartane-type glycoside of the present invention has a VEGF production promoting activity in human epidermal keratinocytes, and hence is considered to exert effects such as improvement of viability of endothelial cells and promotion of vascularization (Heidemarie Rossiter, Caterina Barresi, Johannes Pammer, Michael Rendl, Jody Haigh, Erwin F. Wagner, and Erwin Tschachler. Loss of Vascular Endothelial Growth Factor A Activity in Murine Epidermal Keratinocytes Delays Wound Healing and Inhibits Tumor Formation, Cancer research 64, 3508-3516, 2004) and to be useful for healing of wound, improvement of skin color, hair growing/hair restoration, improvement of hair firmness and elasticity, and the like.

Therefore, the cycloartane-type glycoside of the present invention can be used as a VEGF production promoter or a hair quality improver and can be used for manufacturing a VEGF production promoter or a hair quality improver. The VEGF production promoter may be: a pharmaceutical agent, a quasi-drug, a cosmetic, or a food for humans or animals, which can exert effects such as healing of wound, improvement of skin color, hair growing/hair restoration, and improvement of hair firmness and elasticity; or a material to be blended in the pharmaceutical agent or the like. In addition, in the present invention, the expression "improvement of hair quality" refers to hardening and/or strengthening the nature of hair, and/or imparting firmness and elasticity. The hair quality improver may be a pharmaceutical agent, a quasi-drug, a cosmetic, or a food for humans or animals, or a material to be blended in the pharmaceutical agent or the like.

Further, the cosmetic and food encompass a cosmetic, a food for beauty, a food for a patient, or a functional food such as a food for specified health use which has concepts of promotion of VEGF production, improvement of skin color, hair growing/hair restoration, improvement of hair quality, and the like, and shows the concepts, if necessary.

The administration form of the pharmaceutical agent containing the cycloartane-type glycoside of the present invention includes, for example, oral administration such as a tablet, a capsule, granules, powder, a syrup, or the like, or parenteral administration such as an intravenous injection, an intramuscular injection, a suppository, an inhalant, a transdermally absorbable drug, an eye drop, a nasal drop, an external preparation, or the like. Further, in order to prepare pharmaceutical preparations of such various dosage forms, the cycloartane-type glycoside of the present invention may be used singly or in appropriate combination with any other pharmaceutically acceptable excipient, binder, extender, disintegrator, surfactant, lubricant, dispersant, buffer agent, preservative, corrigent, flavoring agent, coating, carrier, diluent, or the like. In the case where the cycloartane-type glycoside of the present invention is used as the pharmaceutical preparation, in general, the content of the compound in the preparation is preferably 0.00001 to 50 mass %, more preferably 0.0001 to 10 mass %.

For example, the dose of the pharmaceutical agent per adult per day is preferably 0.0003 to 3,000 mg, more preferably 0.003 to 300 mg in terms of the cycloartane-type glycoside.

The form of the food containing the cycloartane-type glycoside of the present invention includes the same form as that of the above-mentioned preparation for oral administration (such as a tablet, a capsule, or a syrup).

In order to prepare foods having various forms, the cycloartane-type glycoside of the present invention may be used singly or in appropriate combination with another food material, a solvent, a softener, an oil, an emulsifier, a preservative, a flavoring agent, a stabilizer, a colorant, a UV absorber, an antioxidant, a moisturizer, a thickener, or the like. In general, the content of the cycloartane-type glycoside in the food is preferably 0.00001 to 100 mass %, more preferably 0.0001 to 70 mass %.

Further, examples of the quasi-drug and cosmetic containing the cycloartane-type glycoside of the present invention include an external preparation for skin, a detergent, a make-up cosmetic, and a cosmetic for scalp hair. According to usage, the quasi-drug and cosmetic may be provided in various dosage forms such as a lotion, an emulsion, a gel, a cream, an ointment, powder, and granules. The quasi-drugs and cosmetics in those various dosage forms may each be prepared using the cycloartane-type glycoside of the present invention singly or in appropriate combination with an oily component, a moisturizer, powder, a dye, an emulsifier, a solubilizer, a detergent, a UV absorber, a thickener, a drug, a flavoring agent, a resin, an anti-bacterial and anti-fungal agent, a plant extract, or an alcohol, which may be blended in a quasi-drug, a skin cosmetic, a cosmetic for scalp hair, or a cleanser. In general, the content of the cycloartane-type glycoside in the quasi-drug or cosmetic is preferably 0.00001 to 100 mass %, more preferably 0.0001 to 70 mass %.

Further, a subject to whom the cosmetic, pharmaceutical agent, or quasi-drug is applied is not particularly limited as long as the subject requires the product. However, the subject is preferably a human who requires promotion of production of VEGF or improvement of hair quality such as hardening and/or strengthening of hair nature and/or imparting firmness and elasticity.

EXAMPLES

Example 1

Preparation of Cycloartane-Type Glycoside from Root of *Cimicifuga simplex*

700 mL of 99.5% ethanol were added to 70 g of a shredded product of the root of *Cimicifuga simplex* (produced in Shaanxi, China), and extraction was carried out at room temperature for 10 days, followed by filtration, to thereby obtain an extract. The extract was concentrated under reduced pressure, and the solvent was distilled off. Subsequently, 2.35 g of the resultant solid matter was subjected to liquid-liquid distribution with ethyl acetate-water, and the ethyl acetate layer was concentrated, to thereby obtain 1.86 g of solid matter. The solid matter was charged to a silica gel column, and elution was carried out with a hexane-ethyl acetate mixed solvent and subsequently methanol, to collect three fractions. 0.9 g of the methanol eluted fraction (fraction 3, 1.39 g) was charged to a silica gel column again, and elution was carried out with a chloroform-methanol mixed solvent, to thereby obtain 12 fractions (3a to 3l). Fraction 3e (0.1 g) was fractionated by ODS-HPLC (acetonitrile-watermixed solvent), to collect eight fractions (3e-1 to 8). A component in fraction 3e-6 was isolated as 24-epi-7,8-didehydrocimigenol-3-xyloside (8.6 mg).

In the same manner as above, fraction 3f (0.17 g) was fractionated by ODS-HPLC (acetonitrile-water mixed solvent), to collect ten fractions (3f-1 to 10). Of the fractions, fraction 3f-2 was isolated as cimicifugoside H-1 (7.9 mg), and fraction 3f-8 was isolated as 7,8-didehydro-24-O-acetylhydroshengmanol-3-O-β-xyloside (5.5 mg).

Example 2

Effect on Production of VEGF (1) Materials and Method

Normal human newborn preputial epidermal keratinocytes (Kurabo Industries Ltd.: frozen NHEK (F) Lot. No. 061130-902) were used in a test. The cells were inoculated into three six-well microplates at $2 \times 10^4$ cells/mL per well. Culture was carried out in Defined keratinocyte-SFM (SFM medium, Gibco) under conditions of 2% $CO_2$ and 37° C. After the cell density reached 50 to 60% confluence, the medium was exchanged for additive-free Defined keratinocyte-SFM medium (SFM (−) medium). The cells were conditioned to the SFM (−) medium for 24 hours, and the medium was then exchanged for an SFM (−) medium supplemented with an arbitrary concentration of the triterpenoid saponin obtained in Example 1. Then, the test was started.

It should be noted that a compound-free SFM (−) medium was used as a negative control. 16 hours after the start of the test, the media were collected, and the amounts of VEGF secreted in the supernatants of the cultures were determined using an ELISA kit (R&D Systems). The amount of VEGF produced in the control was defined as 1, and relative values to the control value were used for evaluation.

(2) Results

Table 1 shows the results of the evaluation.

TABLE 1

| Compound | Concentration (μg/mL) | Relative value of secreted VEGF amount |
|---|---|---|
| Control | | 1.00 |
| Compound 1 | 200 | 5.69 |
| | 100 | 3.65 |
| | 20 | 2.19 |
| Compound 2 | 200 | — |
| | 100 | 0.40 |
| | 20 | 2.32 |
| Compound 3 | 200 | 2.82 |
| | 100 | 2.50 |
| | 20 | 1.19 |

Compound 1: 7,8-Didehydro-24-O-acetylhydroshengmanol-3-O-β-xyloside
Compound 2: 24-epi-7,8-Didehydrocimigenol-3-xyloside
Compound 3: Cimicifugoside H-1

Table 1 shows that all the compounds have excellent effects of promoting production of VEGF.

The invention claimed is:

1. A method of promoting VEGF production, comprising applying an external preparation for skin to a subject in need of promoting VEGF production in said subject's skin keratinocytes, the external preparation for skin comprising a VEGF production promoting amount of a cycloartane-type glycoside represented by the following general formula (1):

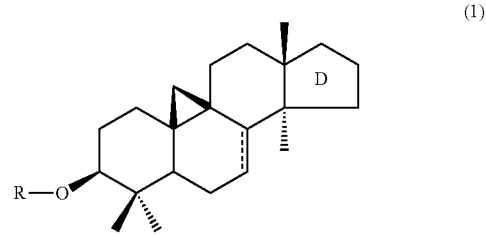

(1)

where R represents a xylose residue or an arabinose residue, and the ring D moiety represents any one of the following moieties a to f:

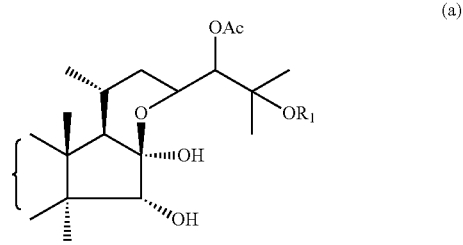

(a)

-continued (b)
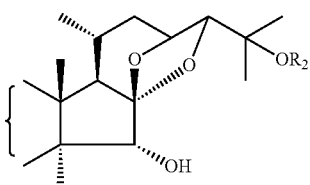

(c)
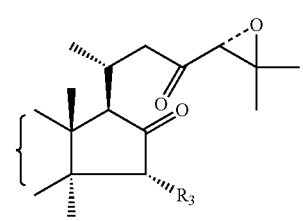

(d)
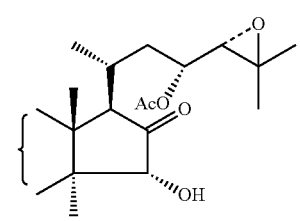

(e)
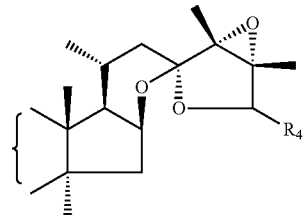

(f)
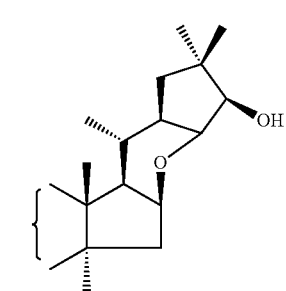

where $R_1$ represents a hydrogen atom or a methyl group, $R_2$ represents a hydrogen atom or an acetyl group, $R_3$ represents a hydrogen atom or a hydroxyl group, $R_4$ represents a hydrogen atom or a hydroxyl group, and Ac represents an acetyl group, and promoting the VEGF production as a result of the applying.

2. A method of improving hair quality, comprising, applying a cosmetic for scalp hair to a subject in need of improving the subject's hair quality, the cosmetic for scalp hair comprising a VEGF production promoting amount of a cycloartane-type glycoside represented by the following general formula (1):

(1)
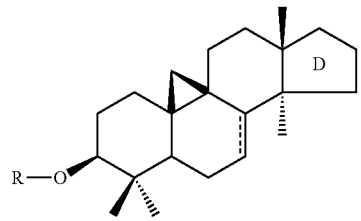

where R represents a xylose residue or an arabinose residue, and the ring D moiety represents any one of the following moieties a to f:

(a)
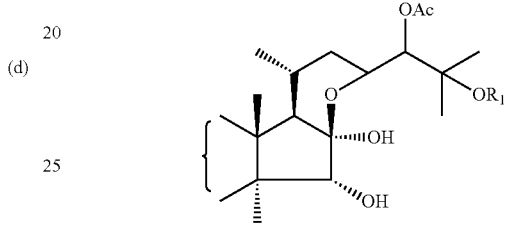

(b)
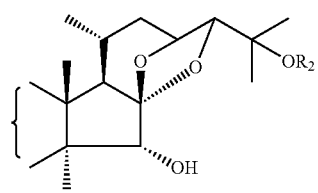

(c)
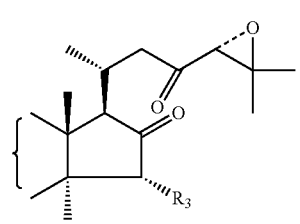

(d)
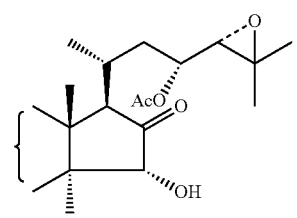

(e)
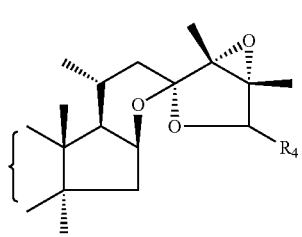

(f)

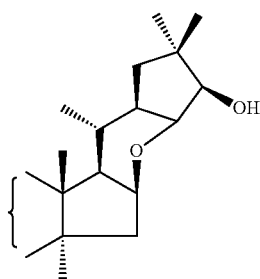

where $R_1$ represents a hydrogen atom or a methyl group, $R_2$ represents a hydrogen atom or an acetyl group, $R_3$ represents a hydrogen atom or a hydroxyl group, $R_4$ represents a hydrogen atom or a hydroxyl group, and Ac represents an acetyl group, and improving the subject's hair quality as a result of the applying.

3. A method of promoting VEGF production, comprising applying an external preparation for skin to a subject in need of promoting VEGF production in said subject's skin keratinocytes, the external preparation for skin comprising a VEGF production promoting amount of a cycloartane-type glycoside represented by the following general formula (1):

(1)

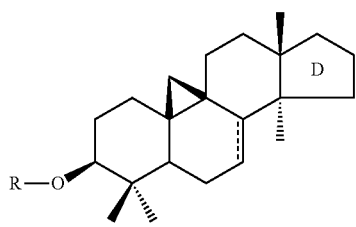

where R represents a xylose residue or an arabinose residue, and the ring D moiety represents any one of the following moieties a to c:

(a)

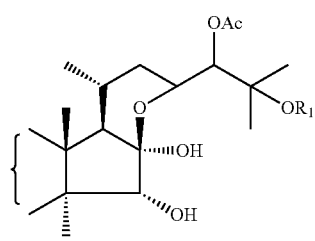

(b)

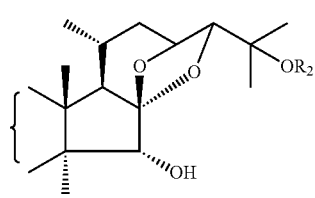

(c)

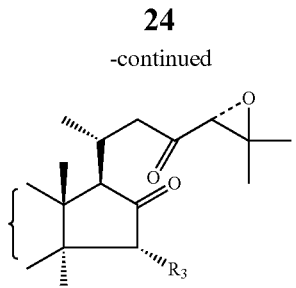

where $R_1$ represents a hydrogen atom or a methyl group, $R_2$ represents a hydrogen atom or an acetyl group, $R_3$ represents a hydrogen atom or a hydroxyl group and Ac represents an acetyl group, and promoting the VEGF production as a result of the applying.

4. A method of promoting VEGF production, comprising applying an external preparation for skin to a subject in need of promoting VEGF production in said subject's skin keratinocytes, the external preparation for skin comprising a VEGF production promoting amount of, a cycloartane-type glycoside represented by the following general formula (1):

(1)

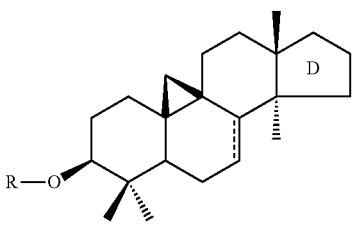

where R represents a xylose residue or an arabinose residue, and the ring D moiety represents the following moiety c:

(c)

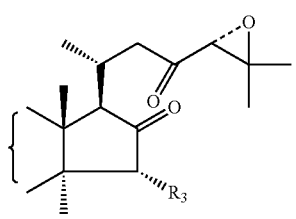

where $R_3$ represents a hydrogen atom or a hydroxyl group, and promoting the VEGF production as a result of the applying.

5. A method of promoting VEGF production, comprising applying an external preparation for skin to a subject in need of promoting VEGF production in said subject's skin keratinocytes, the external preparation for skin comprising a VEGF production promoting amount of a cycloartane-type glycoside selected from the group consisting of 7,8-didehydro-24-O-acetylhydroshengmanol-3-O-β-xyloside, 24-epi-7,8-didehydrocimigenol-3-xyloside, and cimicifugoside H-1, and promoting the VEGF production as a result of the applying.

6. The method of promoting VEGF production according to claim 1, wherein the dose of the cycloartane-type glycoside per day is 0.0003 to 3000 mg.

7. The method of promoting VEGF production according to claim 3, wherein the dose of the cycloartene-type glycoside per day is 0.0003 to 3000 mg.

8. The method of promoting VEGF production according to claim 4, wherein the dose of the cycloartene-type glycoside per day is 0.0003 to 3000 mg.

9. The method of promoting VEGF production according to claim 5, wherein the dose of the cycloartene-type glycoside per day is 0.0003 to 3000 mg.

10. A method of improving hair quality, comprising applying a cosmetic for scalp hair to a subject in need of improvement of the subject's hair quality, the cosmetic for scalp hair comprising a VEGF production promoting amount of a cycloartane-type glycoside represented by the following general formula (1):

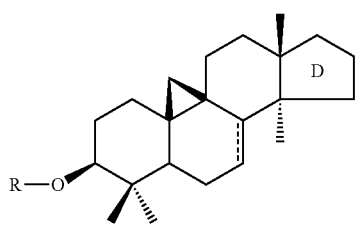

(1)

where R represents a xylose residue or an arabinose residue, and the ring D moiety represents any one of the following moieties a to c:

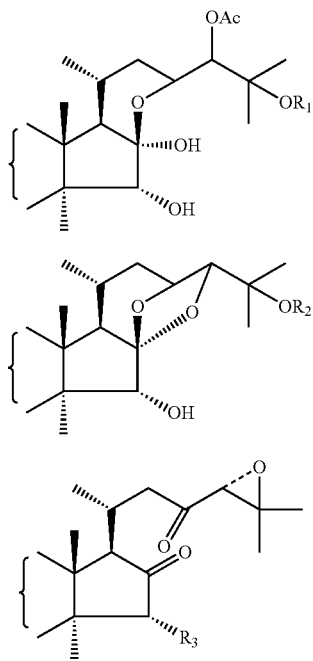

where $R_1$ represents a hydrogen atom or a methyl group, $R_2$ represents a hydrogen atom or an acetyl group, $R_3$ represents a hydrogen atom or a hydroxyl group and Ac represents an acetyl group, and improving the subject's hair quality as a result of the applying.

11. A method of improving hair quality, comprising applying a cosmetic for scalp hair to a subject in need of improving the subject's hair quality, the cosmetic for scalp hair comprising a VEGF production promoting amount of a cycloartane-type glycoside represented by the following general formula (1):

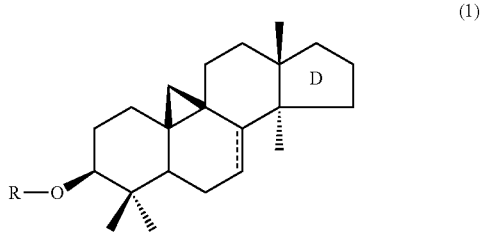

(1)

where R represents a xylose residue or an arabinose residue, and the ring D moiety represents the following moiety c:

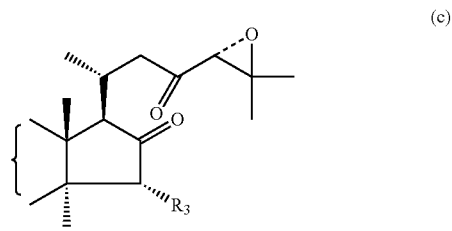

(c)

where $R_3$ represents a hydrogen atom or a hydroxyl group, and improving the subject's hair quality as a result of the applying.

12. A method of improving hair quality, comprising applying a cosmetic for scalp hair to a subject in need of improving the subject's hair quality, the cosmetic for scalp hair comprising a VEGF production promoting amount of a cycloartane-type glycoside selected from the group consisting of 7,8-didehydro-24-O-acetylhydroshengmanol-3-O-β-xyloside, 24-epi-7,8-didehydrocimigenol-3-xyloside, and cimicifugoside H-1, and improving the subject's hair quality as a result of the applying.

13. The method of improving hair quality according to claim 2, wherein the dose of the cycloartane-type glycoside per day is 0.0003 to 3000 mg.

14. The method of improving hair quality according to claim 10, wherein the dose of the cycloartene-type glycoside per day is 0.0003 to 3000 mg.

15. The method of improving hair quality according to claim 11, wherein the dose of the cycloartene-type glycoside per day is 0.0003 to 3000 mg.

16. The method of improving hair quality according to claim 12, wherein the dose of the cycloartene-type glycoside per day is 0.0003 to 3000 mg.

* * * * *